United States Patent [19]
Redwine et al.

[11] Patent Number: 5,891,121
[45] Date of Patent: *Apr. 6, 1999

[54] ABSORBENT ARTICLES HAVING UNDERGARMENT COVERING COMPONENTS ESPECIALLY SUITED FOR FOLDING AROUND THE EDGES OF AN UNDERGARMENT

[75] Inventors: Nona Jane Redwine, Mason; Robb Eric Olsen; Letha Margie Hines, both of Cincinnati; Eric Patton Weinberger, Fairfield, all of Ohio; Bruce William Lavash, Bad Homburg, Germany

[73] Assignee: The Procter & Gamble Company, Cincinnati, Ohio

[*] Notice: The term of this patent shall not extend beyond the expiration date of Pat. No. 5,584,829.

[21] Appl. No.: 493,515

[22] Filed: Jun. 22, 1995

Related U.S. Application Data

[63] Continuation-in-part of Ser. No. 915,133, Jul. 23, 1992, Ser. No. 96,121, Jul. 22, 1993, Pat. No. 5,584,829, Ser. No. 124,180, Sep. 17, 1993, Ser. No. 192,240, Feb. 4, 1994, Ser. No. 228,337, Apr. 15, 1994, Ser. No. 253,001, Jun. 2, 1994, Pat. No. 5,620,430, Ser. No. 277,733, Jul. 20, 1994, Pat. No. 5,558,663, Ser. No. 279,034, Jul. 22, 1994, Ser. No. 308,188, Sep. 19, 1994, and Ser. No. 391,297, Feb. 3, 1995.

[51] Int. Cl.$^6$ ..................................................... A61F 13/15
[52] U.S. Cl. ........................ 604/387; 604/373; 604/385.1
[58] Field of Search ................................ 604/373, 385.1, 604/385, 2, 387

[56] References Cited

U.S. PATENT DOCUMENTS

| | | |
|---|---|---|
| 2,787,271 | 4/1957 | Clark . |
| 3,397,697 | 8/1968 | Rickard . |
| 4,166,464 | 9/1979 | Korpman . |
| 4,285,343 | 8/1981 | McNair . |
| 4,589,876 | 5/1986 | Van Tilburg . |
| 4,608,047 | 8/1986 | Mattingly . |
| 4,687,478 | 8/1987 | Van Tilburg . |
| 4,692,163 | 9/1987 | Widlund et al. . |
| 4,759,754 | 7/1988 | Korpman . |
| 4,790,838 | 12/1988 | Pigneul et al. . |

(List continued on next page.)

FOREIGN PATENT DOCUMENTS

| | | |
|---|---|---|
| 0 331 018 A1 | 9/1989 | European Pat. Off. . |
| 0 426 235 A2 | 5/1991 | European Pat. Off. . |
| 0 0446 818 A2 | 9/1991 | European Pat. Off. . |
| 0 467 184 A1 | 1/1992 | European Pat. Off. . |
| 0 511 905 A1 | 11/1992 | European Pat. Off. . |
| 0 539 032 A1 | 4/1993 | European Pat. Off. . |
| 40-36391 | 12/1965 | Japan . |
| 236101 | 10/1993 | New Zealand . |
| 2 168 253 A | 6/1986 | United Kingdom . |
| 2 262 235 A | 6/1993 | United Kingdom . |
| WO 92/07535 | 5/1992 | WIPO . |
| WO 93/01785 | 2/1993 | WIPO . |
| WO 93/01786 | 2/1993 | WIPO . |
| WO 93/06805 | 4/1993 | WIPO . |
| WO 95/03025 | 7/1994 | WIPO . |
| WO 95/08311 | 9/1994 | WIPO . |
| WO 95/03765 | 2/1995 | WIPO . |

*Primary Examiner*—Robert A. Clarke
*Attorney, Agent, or Firm*—Jeffrey V. Bamber; Steven W. Miller; Jacobus C. Rasser

[57] ABSTRACT

Absorbent articles such as sanitary napkins, panty liners, and incontinence pads are disclosed that have undergarment covering components (or "side wrapping elements") that extend from the main body portion of the absorbent article and automatically fold along the sides of a wearer's panties and provide an alternative to conventional side flaps. The side wrapping elements have at least one zone of extensibility and a region therein that is stiffer and less extensible than the zone of extensibility. The absorbent article preferably comprises at least three regions with different bending moduli to control the location of the absorbent article about which the side wrapping elements will bend.

10 Claims, 7 Drawing Sheets

U.S. PATENT DOCUMENTS

| | | |
|---|---|---|
| 4,891,258 | 1/1990 | Fahrenkrug . |
| 4,900,320 | 2/1990 | McCoy .................................. 604/387 |
| 4,911,701 | 3/1990 | Mavinkurve . |
| 4,917,697 | 4/1990 | Osborn et al. . |
| 4,940,462 | 7/1990 | Salerno . |
| 4,950,264 | 8/1990 | Osborn . |
| 5,007,906 | 4/1991 | Osborn et al. . |
| 5,009,653 | 4/1991 | Osborn . |
| 5,037,417 | 8/1991 | Ternstrom et al. . |
| 5,125,918 | 6/1992 | Seidy . |
| 5,129,893 | 7/1992 | Thoren . |
| 5,267,992 | 12/1993 | Van Tilburg . |
| 5,281,209 | 1/1994 | Osborn et al. . |
| 5,324,278 | 6/1994 | Visscher et al. . |
| 5,344,416 | 9/1994 | Niihara ................................. 604/387 |
| 5,346,486 | 9/1994 | Obsborn III et al. ............... 604/385.2 |
| 5,354,400 | 10/1994 | Lavash et al. . |
| 5,389,094 | 2/1995 | Lavash et al. . |
| 5,429,630 | 7/1995 | Beal et al. . |
| 5,429,633 | 7/1995 | Davis et al. . |
| 5,518,801 | 5/1996 | Chappell et al. . |
| 5,558,663 | 9/1996 | Weinberger et al. . |
| 5,584,829 | 12/1996 | Lavash et al. ........................ 604/387 |

ABSORBENT ARTICLES HAVING UNDERGARMENT COVERING COMPONENTS ESPECIALLY SUITED FOR FOLDING AROUND THE EDGES OF AN UNDERGARMENT

CROSS-REFERENCE TO RELATED APPLICATIONS

This is a continuation-in-part of the following U.S. patent applications: Ser. No. 07/915,133 filed Jul. 23, 1992, in the name of Osborn, et al.; Ser. No. 08/096,121 filed Jul. 22, 1993, in the name of Lavash, et al. now U.S. Pat. No. 5,584,829; Ser. No. 08/124,180 filed Sep. 17, 1993, in the name of Mansfield, et al.; Ser. No. 08/192,240 filed Feb. 4, 1994, in the name of Osborn, et al.; Ser. No. 08/228,337 filed Apr. 15, 1994, in the name of Randall, et al.; Ser. No. 08/253,001 filed Jun. 2, 1994, in the name of Lavash, et al. now U.S. Pat. No. 5,620,430; Ser. No. 08/277,733 filed Jul. 20, 1994, in the name of Weinberger, et al. now U.S. Pat. No. 5,558,663; Ser. No. 279,034 filed Jul. 22, 1994, in the name of Hammons, et al.; Ser. No. 08/308,188 filed Sep. 19, 1994, in the name of Hammons, et al.; and Ser. No. 08/391,297 filed Feb. 3, 1995, in the name of Osborn, et al.

FIELD OF THE INVENTION

The present invention relates to absorbent articles such as sanitary napkins, panty liners, and incontinence pads. More particularly, the present invention relates to absorbent articles that have undergarment covering components (or "side wrapping elements") that fold or wrap the sides of a wearer's undergarments when the undergarments are pulled up, providing an alternative to conventional side flaps.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body. Sanitary napkins both with and without side flaps (or wings) are disclosed in the literature and are available in the marketplace.

Generally when sanitary napkins are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are generally effective for preventing exudates from soiling the edges of the wearer's panties.

Sanitary napkins having flaps of various types are disclosed in U.S. Pat. No. 5,267,992 entitled "Shaped Sanitary Napkin With Flaps", which issued Dec. 7, 1993; U.S. Pat. No. 4,687,478, entitled "Shaped Sanitary Napkin With Flaps", which issued to Van Tilburg on Aug. 18, 1987; U.S. Pat. No. 4,608,047, entitled "Sanitary Napkin Attachment Means", which issued to Mattingly on Aug. 26, 1986; U.S. Pat. No. B1 4,589,876, entitled "Sanitary Napkin", which issued to Van Tilburg, Certificate of Reexamination issued Apr. 27, 1993; U.S. Pat. No. 4,285,343, entitled "Sanitary Napkin", which issued to McNair on Aug. 25, 1981; U.S. Pat. No. 3,397,697, entitled "Disposable Sanitary Shield For Undergarments", which issued to Rickard on Aug. 20, 1968; and, U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, some women find applying sanitary napkins having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. As a result, some women still prefer a sanitary napkin without flaps. In addition, some women who generally prefer a sanitary napkin with flaps, occasionally (such as during periods of light flow) prefer a sanitary napkin without flaps. Therefore, there is a need for a sanitary napkin which provides an alternative to sanitary napkins having conventional side flaps while still providing the protection of side flaps.

Several variations of sanitary napkins having conventional flaps that attempt to solve some, but not all of these problems are disclosed in the patent literature. For example, U.S. Pat. No. 4,911,701 issued to Mavinkurve discloses a sanitary napkin having elastic strands for providing a greater convex shape to the body-facing portion of the central absorbent and for enabling adhesive-free placement of the flaps of a winged napkin embodiment into a pair of panties. The sanitary napkin described in the Mavinkurve patent, however, still appears to require the user to manipulate the flaps (by first flipping the flaps upward and then placing the flaps in her panties and flipping the flaps back down) since the flaps appear to be pre-disposed to be in a downward folded condition. The Mavinkurve patent also requires that individual elastic strands be attached in a contracted condition to the central absorbent portion of the napkin and/or to its wings or flaps. The napkins described in the Mavinkurve patent can, therefore, be difficult and expensive to manufacture.

U.S. Pat. No. 5,125,918 issue to Seidy is directed to sanitary napkins having flaps with a "specially designed" resilient hinge means for disposing the flaps in an acute angular relation with the undergarment facing side of the absorbent element of the sanitary napkin. The resilient hinge, however, is described as one which tends to return to its original position after deformation. U.S. Pat. Nos. 5,154,715 and 5,221,275 issued to Van Iten are directed to absorbent articles, such as sanitary napkins, that have a "clasp means" for fastening the absorbent article to an adjacent undergarment. The clasp means of the Van Iten patents includes two relatively stiff portions (that are more rigid than the absorbent pad) which are joined together by a hinge which permits bending of one portion relative to the other portion. At least one of the portions has an arcuate portion that is designed to pivot on the hinge and "forcefully press" the undergarment towards the first member when the absorbent article is worn. Such a clasp may, thus, tend to forceably alter the configuration of the undergarment. Further, the stiffness of the clasp means may tend to make the absorbent article uncomfortable to wear.

U.S. Pat. No. 4,940,462 issued to Salerno discloses a sanitary napkin with longitudinally expandable flaps. The flaps are designed to fold over the exterior of the wearer's panty and then to expand to conform with the contour of the panties. The sanitary napkin described in the Salerno patent, however, appears to require conventional adhesive fasteners to retain the flaps in place on the underside of the wearer's panties.

Thus, a need exists for an absorbent article, such as a sanitary napkin, that is provided with an alternative to conventional flaps. In particular, a need exists for a sanitary napkin which provides the protection from soiling of conventional flaps and which can conveniently and efficiently solve the problems caused when attempting to attach conventional flaps to the underside of the wearer's panties.

It is, therefore, an object of the present invention to provide an absorbent article, such as a sanitary napkin, that is able to provide coverage to the wearer's panties to reduce side soiling (i.e., staining of the edges of the panty crotch) without the use of conventional flaps.

It is another object of the present invention to provide an absorbent article, such as a sanitary napkin, that automatically folds around the sides of the wearer's panties by the simple action of the wearer pulling up her panties.

It is still another object of the present invention to provide an absorbent article, such as a sanitary napkin, that is able to fold around the sides of the wearer's panties and stay without providing flaps having panty fasteners thereon, and without attaching separate elastic strands to the sanitary napkin.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has a pair of undergarment covering components (or "side wrapping elements") that provide coverage to the wearer's panties to reduce staining of the edges of the panty crotch (or "side soiling") without the use of conventional flaps.

The sanitary napkin comprises a main body portion comprising a liquid pervious topsheet, a liquid impervious backsheet joined to the topsheet, and an absorbent core positioned between the topsheet and the backsheet. The side wrapping elements comprise a pair of flexible elements that extend beyond the crotch edge portions of the wearer's undergarment. The side wrapping elements are preferably integral extensions of components of the main body portion, such as the topsheet and backsheet. In other embodiments, however, the side wrapping elements can be separate components that are joined to the garment-facing side of the main body portion, preferably inboard of the longitudinal side edges of the main body portion. The side wrapping elements are preferably each provided with at least one zone of extensibility, and preferably with two spaced apart zones of extensibility. The zones of extensibility can be extensible in the longitudinal direction, the transverse direction, in a direction between the longitudinal and transverse directions, or in several directions. The zones of extensibility are regions of the side wrapping elements that have a greater range of extension than the adjacent regions of the side wrapping elements. The side wrapping elements preferably comprise at least one zone of extensibility on each side of the transverse centerline of the side wrapping elements and a stiffer, less extensible intermediate region along the transverse centerline of the side wrapping elements.

The sanitary napkin of the present invention preferably comprises at least three regions having different bending properties. These three regions preferably comprise at least a first region, a second region, and a third region. The first region is preferably located in the main body portion inboard of the longitudinal side edges of the main body portion, and has a first bending modulus. The second region preferably comprises at least a portion of the intermediate region of the side wrapping elements, and has a second bending modulus. The third region is preferably located in a region along the juncture of the side wrapping elements with the main body portion, and has a third bending modulus. The first region preferably comprises the portion of the main body portion containing the absorbent core. The bending modulus of the first region of the sanitary napkin is preferably the highest of the bending moduli. The bending modulus of the third region of the sanitary napkin along the juncture of the side wrapping elements with the main body portion is preferably the lowest, and the bending modulus of the second region of the sanitary napkin in the intermediate region of the side wrapping elements is preferably between that of the first and third regions.

The preferred side wrapping elements utilized on the sanitary napkin of the present invention have improved resistance to crumpling and other types of transverse deformation than a similar side wrapping element would have if it were made of the same material and was provided with extensibility along its full length. The stiffer, less extensible intermediate region located along the transverse centerline of the side wrapping elements provides the side wrapping elements with the improved resistance to bending and crumpling. The low bending modulus of the third region provides a hinge about which the side wrapping elements may fold relative to the main body portion of the sanitary napkin. The improved resistance to crumpling ensures that the side wrapping elements will fold over the elasticated sides of the wearer's panties, and will resist crumpling when the wearer's thighs apply compressive forces on the distal edges of the side wrapping elements and when shearing forces are applied by movements that cause the wearer's thighs rub against the side wrapping elements. The fact that the side wrapping elements have crumpling resistance and zones of extensibility allows the side wrapping elements to automatically fold around (or along) the crotch edge portions of the wearer's undergarment toward the underside of the undergarment and to remain so folded over the crotch edge when the absorbent article is placed in an undergarment and the undergarment is pulled up adjacent the wearer's body. The zones of extensibility and difference in stiffness of the various regions of the sanitary napkin provide a mechanism for controlling the manner and location of folding of the side wrapping elements.

The sanitary napkin of the present invention provides an alternative to sanitary napkins having conventional side flaps for several reasons. The side wrapping elements do not extend far enough outward beyond the side edges of the wearer's panties to cause any inconvenience to the wearer. The side wrapping elements require no action on the part of the wearer to fold the side wrapping elements under her panties or to attach the same to her panties. The side wrapping elements stay in place well enough to cover the side edges of the wearer's panties without affixing them underneath the wearer's panties. In alternative embodiments, however, the sanitary napkin may be provided with a fastener, such as a pressure sensitive adhesive, for additional security during vigorous motions by the wearer. The adhesive fastener may be provided on the garment-facing side of the main body portion and on the garment-facing side of the side wrapping elements.

BRIEF DESCRIPTION OF THE DRAWINGS

While the specification concludes with claims particularly pointing out and distinctly claiming the subject matter which is regarded as forming the present invention, it is believed that the invention will be better understood from the following description when taken in conjunction with the accompanying drawings in which:

DETAILED DESCRIPTION OF THE INVENTION

Figure 1:
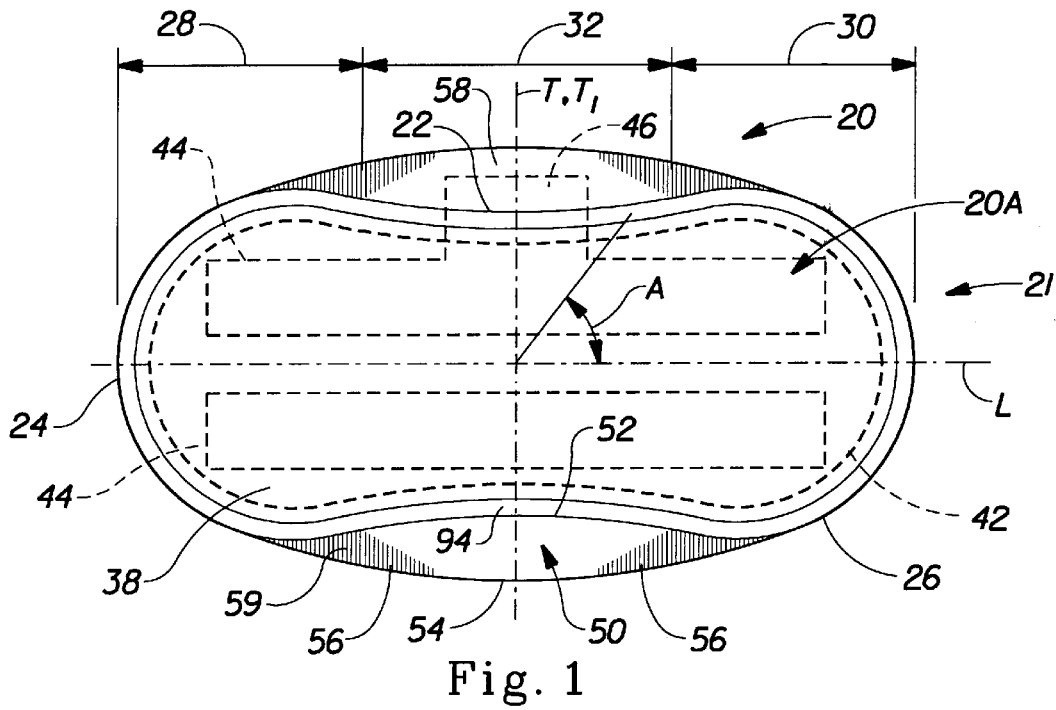
FIG. 1 is a top plan view of one embodiment of the sanitary napkin of the present invention.
Figure 2:
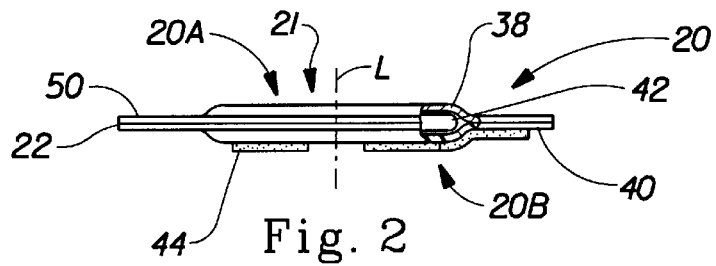
FIG. 2 is an end view of the sanitary napkin shown in FIG. 1 shown with a portion of the topsheet cut away to show the absorbent core.
Figure 3:
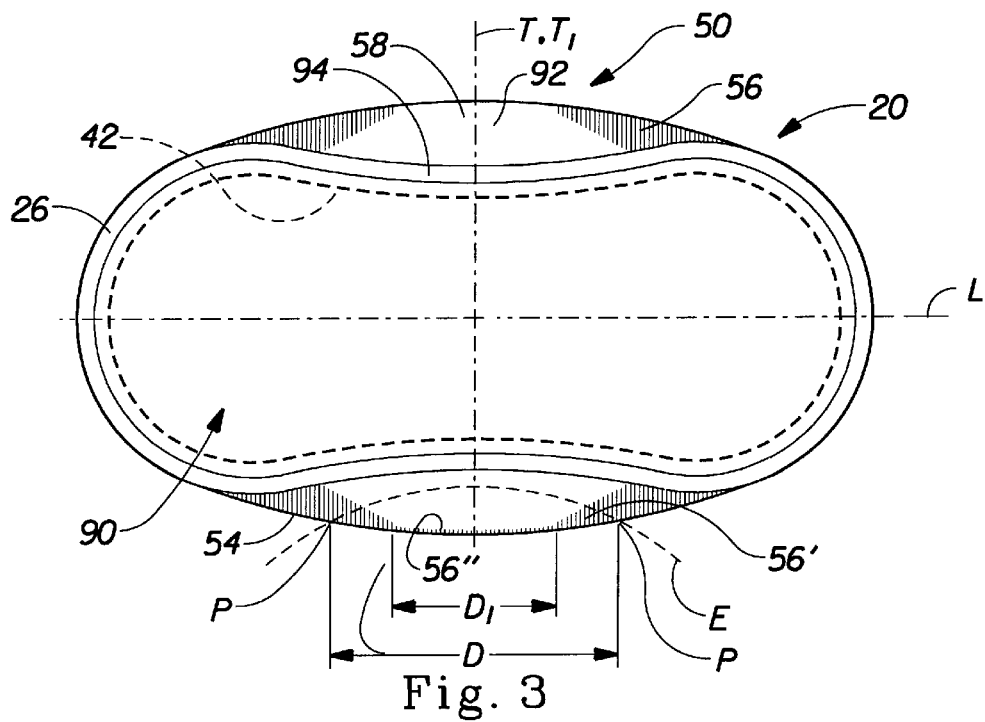
FIG. 3 is another top plan view of the sanitary napkin shown in FIG. 1 that shows the properties of the various regions of the sanitary napkin.

The present invention relates to absorbent articles, such as sanitary napkins, panty liners, and incontinence pads. More particularly, the present invention relates to absorbent articles that have a main body portion 21 and a pair of side wrapping elements 50 that automatically fold along and wrap the sides of the wearer's panties when the wearer places the sanitary napkin in her panties and pulls her panties up. FIGS. 1–3 show one preferred embodiment of a disposable absorbent article of the present invention, sanitary napkin 20.

The sanitary napkin 20 (and the main body portion 21 thereof) has two surfaces, a liquid pervious body-contacting surface or "body surface" 20A and a liquid impervious garment surface 20B. The sanitary napkin 20 is shown in FIG. I as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral"used herein, are interchangeable, and refer to a line, axis or direction which lies within the plane of the sanitary napkin 20 that is generally perpendicular to the longitudinal direction.

FIG. 1 shows that the main body portion 21 of the sanitary napkin 20 comprises the portion of the sanitary napkin without the side wrapping elements. The main body portion 21 has two spaced apart longitudinal edges 22, two spaced apart transverse or end edges (or "ends") 24, which together form the periphery 26 of the main body portion. The main body portion also has two end regions, which are designated first end region 28 and second end region 30. A central region 32 is disposed between the end regions 28 and 30. The end regions 28 and 30 extend outwardly in the longitudinal direction from the edges of the central region 32 about ⅛ to about ⅓ of the length of the main body portion. A detailed description of the characteristics of a central region and two end regions for a sanitary napkin is contained in U.S. Pat. No. 4,690,680 issued to Higgins on Sep. 1, 1987.

The main body portion 21 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of a sanitary napkin of an intermediate thickness. The main body portion 21 of the sanitary napkin 20 may also be relatively flexible, so that it is comfortable for the wearer. It should be understood that the sanitary napkin shown is merely one embodiment, and that the present invention is not limited to absorbent articles of the type or having the specific configurations shown in the drawings.

FIG. 2 shows the individual components of the main body portion 21 of the sanitary napkin 20 of the present invention. The main body portion 21 of the sanitary napkin preferably comprises at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations).

Several preferred sanitary napkins having main body portions that can be provided with side wrapping elements and adapted to have the regions with the different properties specified herein are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. No. 4,950,264, "Thin, Flexible Sanitary Napkin" issued to Osborn on Aug. 21, 1990; U.S. Pat. No. 5,308,346, "Elasticized Sanitary Napkin" issued to Sneller, et al. on May 3, 1994; U.S. patent application Ser. No. 08/096,121 entitled "Absorbent Articles Having Panty Covering Components That Naturally Wrap the Sides of Panties" filed Jul. 22, 1993, in the name of Lavash, et al. (PCT Publication No. WO 94/02096, published Feb. 3, 1994); U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. (PCT Publication No. WO 95/07675, published Mar. 23, 1995); and U.S. patent application Ser. No. 08/277,733 entitled "Absorbent Articles Having Undergarment Covering Components With Zones of Extensibility" filed Jul. 20, 1994 in the name of Weinberger, et al. (PCT Publication No. WO 95/03025, published Feb. 2, 1995). The main body portion 21 of the sanitary napkin may also be comprised of one or more extensible components such as those sanitary napkins, and the like described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993).

FIGS. 1 and 2 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 26. The topsheet 38 is joined to the backsheet 40. The topsheet 38 and backsheet 40 can be joined in any suitable manner known in the art for this purpose. Preferably, the topsheet 38 and backsheet 40 are sealed at least around the periphery of the main body portion 21 by a peripheral crimp seal 48 where the topsheet 38 and backsheet 40 are densified by the application of pressure or heat and pressure.

The sanitary napkin 20 shown in FIGS. 1 and 2 also comprises a pair of side wrapping elements 50 that extend laterally outward beyond the longitudinal side edges 22 of the main body portion 21 from their proximal edges 52 to their distal edges 54. The side wrapping elements 50 can be of any suitable size and shape. Preferably, however, the distal edges 54 of the side wrapping elements extend outward beyond the longitudinal side edges 22 of the main body portion 21, a distance of less than or equal to one-half the width of the main body portion. The side wrapping elements 50 of the present invention may have the dimensions and characteristics set forth for the panty covering components in the aforementioned U.S. patent application Ser. Nos. 08/096,121, 08/124,180, and 08/277,733 filed in the names of Lavash, et al., Mansfield, et al., and Weinberger, et al., respectively, which are incorporated by reference herein.

The side wrapping elements 50 can be joined to the main body portion 21 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, as shown in FIGS. 1 and 2, the side wrapping elements 50 are integral with the main body portion 21 (that is, integral extensions of the topsheet 38 and backsheet 40). In other alternate embodiments, the side wrapping elements 50 can comprise two separate components that are joined to the garment-facing side of the main body portion 21. In such alternative embodiments, the side wrapping elements 50 are preferably otherwise unattached to the garment-facing side of the main body portion 21 of the sanitary napkin 20 between the points where they are attached to the main body portion and the longitudinal side edges 22 of the main body portion. The side wrapping elements 50 in these latter embodiments can be joined to the garment-facing side of the main body portion 21 by any suitable attachment mechanism. Suitable attachment mechanisms include, but are not limited to adhesives, and the like. In other embodiments, instead of comprising two separate components, the side wrapping elements 50 can comprise a single component that is joined to the main body portion (which may be referred to as a "panty covering component" or "undergarment covering component"). In still other embodiments, each side wrapping element 50 can comprise more than one component.

The side wrapping elements 50 can be made from many of the materials known in the art for use in the construction of sanitary napkins. The side wrapping elements 50 in the embodiment shown in FIGS. 1 and 2 preferably comprise a laminate of at least two materials. Preferably, the side wrapping elements 50 comprise a laminate comprising a three dimensional apertured formed film and a liquid impervious backing, such as a polyethylene film backsheet material. The apertured formed film is preferably the topsheet material made in accordance with U.S. Pat. No. 4,342,314 issued to Radel, et al. and U.S. Pat. No. 4,463,045 issued to Ahr, et al. and marketed on sanitary napkins by The Procter & Gamble Company under the name DRI-WEAVE. The laminate has been found to be suitable where it is desirable to perform further mechanical operations on the laminate to provide zones of greater extensibility in selected regions of the laminate.

The side wrapping elements 50 may also comprise additional layers if desired. For instance, the body-facing side of the side wrapping elements 50 may be provided with an optional soft coverstock material, such as a soft nonwoven web, to provide improved tactile properties adjacent the wearer's skin. Nonwoven webs suitable for use as a coverstock material include a product known as Spunbond PE, which was obtained from Polybond, Incorporated of Waynesboro, Va., and a product known as COROLIND PE, which was obtained from Corovin GMBH of Germany. In addition, if desired, the side wrapping elements 50 may comprise other optional layers, such as layers to increase the stiffness of the side wrapping elements 50, or various regions thereof. Optional stiffening layers can comprise materials that include, but are not limited to foams and scrims. The optional stiffening layers can be positioned in any suitable location in the side wrapping elements 50 of the sanitary napkin, such between the portions of the topsheet and backsheet that form the side wrapping elements. Preferably, however, such optional stiffening layers are provided on the garment-facing side of the side wrapping elements for ease of manufacture.

In the preferred embodiment shown in FIGS. 1 and 2, the side wrapping elements 50 each have at least one, and preferably have two zones of extensibility 56 therein. The zones of extensibility 56 can be primarily extensible in the longitudinal direction (that is, they are extensible more in the longitudinal direction than in the transverse direction). In other embodiments, the zones of extensibility 56 can be primarily extensible in the transverse direction, or in any direction between the longitudinal direction and the transverse direction, or in more than one direction. The side wrapping elements 50 shown in FIGS. 1 and 2 have zones of extensibility 56 that are primarily extensible in the longitudinal direction. The extensibility of all the zones of extensibility 56 of the side wrapping elements 50 can be in the same direction. In alternative embodiments, one or more of the zones of extensibility 56 may be extensible in a different direction.

The zones of extensibility 56 are preferably capable of extending between about 20% and about 80%, more preferably between about 40% and about 60%, and most preferably about 50% under the forces associated with folding the side wrapping elements 50 around the side edges of the crotch of a pair of panties. Preferably, the zones of extensibility 56 are capable of such extension under forces of less than about 100–200 grams$_f$ per inch (about 40–80 g$_f$/cm), more preferably under forces of less than about 50 grams$_f$ per inch (about 20 g$_f$/cm). The zones of extensibility 56 are also preferably extensible without being elasticized or elasticated (that is, where separate elastic bands are stretched and attached to the side wrapping elements 50 in an extensible condition). Further, any inherent elasticity in the zones of extensibility 56 (that is, any tendency of the material comprising the zones of extensibility to return to its original dimension) is preferably generally relatively low to nonexistent. Preferably, the zones of extensibility 56 exhibit a return force of less than or equal to about 100 grams$_f$ when extended.

FIG. 3 shows the preferred locations for the zones of extensibility 56 and the manner in which the preferred amounts of extensibility in the zones of extensibility 56 are determined. The curved line, E, in FIG. 3 represents the location where the edges of a wearer's panty crotch might lie when the sanitary napkin 20 is placed in a pair of panties prior to the side wrapping elements 50 being folded around the edges of the crotch of the panties. The panty edges E cross the distal edge 54 of the side wrapping element 50 at two points, designated P. The zones of extensibility 56 should be located where the panty edges E cross the distal edges 54 of the side wrapping elements 50. The distance, D, between these two points P varies depending on the size and style of panties. A representative distance D is equal to about 85 mm. FIG. 3 also shows portions 56' of the zones of extensibility 56 that are disposed longitudinally inboard of the points P (that is, toward the transverse centerline $T_1$ of the side wrapping elements). In order to fit a wide variety of panty sizes and styles, it is preferred that each of the portions 56' of the zones of extensibility 56 between points P is capable of extending greater than or equal to about 10–15 mm under the aforementioned forces, and that the combined extensibility in these portions for each side wrapping element 50 is greater than or equal to about 20–30 mm. The longitudinal distance between the points within each of the zones of extensibility 56 that are on opposite sides of the transverse centerline of a side wrapping element 50 is preferably between about 20 mm and about 150 mm, and more preferably is between about 30–130 mm, and most preferably is between about 30–100 mm.

It is possible, however, that portions of the zones of extensibility 56 that are on opposite sides of the transverse centerline T1 of a side wrapping element can abut each other at least at certain areas so that there is no separation between the zones of extensibility 56. For example, the bottom portion of FIG. 3 shows that the zones of extensibility 56 may be extended toward the transverse centerline T1 in certain areas, such as extensions 56" that run along the distal edge 54 of the side wrapping elements 50. The extensions 56" provide additional extensibility along the distal edge 54 of the side wrapping elements 56 (where additional extensibility can be beneficial). In addition, since the extensions 56" are relatively narrow (when measured in the transverse direction), they will not substantially alter the desired stiffness of the different regions of the sanitary napkin.

The side wrapping elements 50 can be provided with zones of extensibility 56 in a non-limiting number of different manners. The side wrapping elements 50 may, for example, comprise a material that is substantially inextensible under the forces described above. The side wrapping elements 50 can then have portions which are altered so that they are provided with extensible regions for the zones of extensibility 56. The extensible regions can be created in any suitable manner, including but not limited to mechanically straining, corrugating, "ring rolling", heating and deforming, subjecting portions of the side wrapping elements 50 to compression between mating plates, forming a network of distinct regions therein to provide portions of the side wrapping elements with the properties of a Structural Elastic-Like Film without added elastic materials (or the "SELFing" process described in U.S. patent application Ser. No. 08/203,087 filed in the name of Chappell, et al. on Feb. 28, 1994 (PCT Publication No. WO 95/03765, published Feb. 9, 1995). This process is described in greater detail below in conjunction with FIGS. 10–10C, and several of the figures which follow).

In other embodiments, the extensible regions of the side wrapping elements can be provided by forming the side wrapping elements out of materials having different extensibilities. For example, the side wrapping elements 50 can be comprised of a laminate of an extensible material and a relatively inextensible material. In such an embodiment, the relatively inextensible material can be provided in the configuration of the side wrapping elements. The inextensible material can then have holes cut out where the zones of extensibility 56 are to be located. This inextensible material can then be laminated to the extensible material to form a side wrapping element with zones of extensibility 56 at the locations where the holes were cut out of the inextensible material.

The embodiment shown in FIGS. 1–3 has zones of extensibility 56 formed by ring rolling (or pre-corrugating) two regions of each of the side wrapping elements 50. Suitable methods for ring rolling are described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

The side wrapping elements 50 in the embodiment shown in FIGS. 1–3 are provided with ring rolled corrugations having fold lines (or ridges and valleys) 59, that are oriented generally in the transverse direction. This provides zones of extensibility 56 that are primarily extensible in the longitudinal direction. In other embodiments, the fold lines could be angled away from the longitudinal centerline L. The fold lines 59 can form any angle, A, with the longitudinal centerline, between greater than 0° and less than or equal to 180°. The fold lines 59 in the various possible alternative embodiments can, for example, form an angle of between about 40°–45° with the longitudinal centerline L. In cases in which the fold lines 59 form an angle of less than 45°, the orientation of the extensibility may be primarily in the transverse direction.

The side wrapping elements 50, as shown in FIG. 3, preferably have a trapezoidally-shaped intermediate region or zone 58 located between at least portions of the zones of extensibility 56. This intermediate region 58 preferably has a distal edge portion that forms a portion of the distal edge 54 of the side wrapping elements. However, as shown on the side wrapping element 50 on the bottom of FIG. 3, embodiments can be constructed in which the distal edge portion of the intermediate region 58 may be laterally inboard of the distal edge 54 of the side wrapping elements 50. The length $D_1$ shown in FIG. 3 of the distal edge portion, is preferably at least about 20 mm, and more preferably about 30 mm. The intermediate region 58 is preferably less extensible than the portions of the side wrapping elements 50 that comprise the zones of extensibility 56. The intermediate region 58 provides the side wrapping elements 50 with greater resistance to crumpling so that the side wrapping elements will fold over the panty elastic, rather than crumple, when they are subject to compression by the wearer's thighs.

The configuration and location of the zones of extensibility 56 in the embodiment shown in FIGS. 1–3 is preferred for several reasons. The fact that the zones of extensibility 56 are spaced apart and separated by the stiffener intermediate region 58 provides improved resistance to undesirable crumpling while providing more control over the manner of folding around the edges of the wearer's panties. The side wrapping elements 50 will typically fold at those locations in the zones of extensibility 56 and the intermediate region 58 between the points where the panty edges cross the distal edges 54 of the side wrapping elements 50 that are situated along the panty elastics. The presence of the stiffer intermediate regions 58 makes the side wrapping elements sturdier and capable of more reliable folding than if the side wrapping elements 50 were made entirely extensible and/or were made of materials having the same stiffness over their entire area.

The stiffer intermediate region 58 also helps to maintain panty elastic coverage when the wearer pulls her panties down to check the sanitary napkin 20 for soiling, and then pulls her panties back up. The stiffer material ensures that the side wrapping elements 50 will go back into place in a downwardly folded configuration around the edges of the wearer's panties.

The sanitary napkin 20 of the present invention preferably also comprises a flexible bending zone (or hinge) 94. The bending zone 94 provides at least one axis about which the side wrapping elements 50 may fold relative to the main body portion 21. The side wrapping elements 50 preferably at least initially bend around the edge of the wearer's panties along at least a portion of the bending zone 94. The bending zone 94 is preferably located between at least a portion of the main body portion 21 of the sanitary napkin 20 and the distal edge 54 of the side wrapping elements 50. The bending zone 94 preferably has little to no bending resiliency. As a result, the side wrapping elements 50 will have very little tendency to return to their original extended position after they fold along the edges of the wearer's undergarment. The side wrapping elements 50 with the bending zone 94 described herein preferably function by adapting to the configuration of the edges of the panties unlike clasp structures described in the patent literature which may forcefully alter the configuration of the sides of the wearer's undergarment.

The bending zone 94 can comprise any suitable structure which satisfies these criteria. The bending zone 94 can comprise areas of the sanitary napkin which are densified, scored, areas which are not laminated but are surrounded by laminated regions, and areas which are mechanically deformed, or which are otherwise formed into structures which provide enhanced flexibility. In the preferred embodiment shown in FIG. 1, the bending zone 94 comprises the peripheral seal 48 along the outer edges of the main body portion where the topsheet 38 and backsheet 40 extend beyond the longitudinal edges of the absorbent core 42 and are joined together.

The peripheral seal 48 is provided with enhanced flexibility relative to the absorbent core 42. This is possible because the seal 48 preferably does not contain absorbent material (or contains less absorbent material than the absorbent core). The elimination of this layer of material makes the portion of the sanitary napkin containing the peripheral seal 48 thinner and, thus, more flexible than the portion of the sanitary napkin containing the absorbent core. The peripheral seal 48 is preferably also more flexible than the adjacent intermediate region 58 of the side wrapping element. This is possible in the embodiment shown in FIG. 1 because the peripheral seal 48 comprises a densified region in the extension of the topsheet 38 and backsheet 40. The means for providing the sanitary napkin 20 with a region having enhanced flexibility relative to other portions of the sanitary napkin, however, is not limited to the use of densified regions such as crimped seals. Any other suitable means for providing the sanitary napkin 20 with enhanced flexibility in this region can be used instead of, or in addition to, a crimp seal.

The flexible bending zone 94 may extend completely around the outer perimeter of the main body portion 21 as shown in FIG. 1. In other embodiments, however, the bending zone 94 may only extend around a portion of the perimeter of the main body portion 21. For example, the bending zone 94 may only extend along the juncture between the side wrapping elements 50 and the main body portion 21. The juncture comprises the lines or areas where the side wrapping elements 50 extend from, or are otherwise joined to the main body portion 21 (although it is not necessary that there be a precise line of demarcation between the side wrapping elements and the main body portion). In cases where the bending zone 94 extends along the juncture, as shown in the drawings, the bending zone 94 may extend the entire length of the juncture between the side wrapping elements 50 and the main body portion 21, or only a portion of the length thereof.

The flexible bending zone 94 may be positioned at any suitable location between at least a portion of the main body portion 21 and the distal edge 54 of the side wrapping elements 50. The bending zone 94 can, thus, be located along the juncture of the side wrapping elements 50 and the main body portion 21, in the region of the juncture, or outboard of the juncture. The bending zone 94, thus, need not be immediately adjacent to the longitudinal side edge 22 of the main body portion 21 as shown in FIG. 1. When the bending zone 94 does not comprise a crimp seal, the hinge structure may be disposed outboard of the juncture, and is preferably located where the elasticized side edges of the wearer's panties cross the side wrapping elements.

The flexible bending zone 94 may be provided in any suitable shape. The bending zone 94 may be comprised of linear segments, curvilinear segments, or some regions of the bending zone 94 may be comprised of linear segments, and some regions may be comprised of curvilinear segments. Preferably, the bending zone 94 is configured that the portions thereof that are adjacent to the central region 32 of the main body portion are located at least as close to the longitudinal centerline of the sanitary napkin, and more preferably, closer to the longitudinal centerline L than the portions of the bending zone 94, if any, that are situated adjacent to the end regions 28 and 30 of the sanitary napkin. Most preferably, as shown in FIGS. 1 and 2, the bending zone 94, is preferably concave when looking at the same from the distal edges 54 of the side wrapping elements 50.

The sanitary napkin 20 of the present invention can (as is apparent from the foregoing discussion), be thought of as having several regions with different bending properties, and several regions with different deformation properties (or different extensibility characteristics).

In preferred embodiments, the sanitary napkin 20 has at least three distinct regions with different bending properties. These are shown in FIG. 3. These regions are designated as a first region 90 that has a first bending modulus, a second region 92 that has a second bending modulus, and a third region 94 that has a third bending modulus. Preferably, as shown in FIG. 3, the first region 90 comprises the portion of the main body portion 21 of the sanitary napkin that contains the absorbent core 42. This first region 90 preferably has the highest bending modulus (that is, is the stiffest) of the three regions. The second region 92 preferably comprises the intermediate regions 58 of the side wrapping elements 50. The second region 92 preferably has a bending modulus which is between the bending moduli of the first and third regions, 92 and 94. The third region 94 comprises the bending zone, and is preferably the most flexible of the three regions.

FIG. 3 also shows that the sanitary napkin 20 preferably has at least two distinct regions with different degrees of extensibility under a given force or range of forces (that is, different deformation moduli). These regions comprise the zones of extensibility 56 and the intermediate region 58 located between the zones of extensibility 56. The zones of extensibility 56 are more extensible than the intermediate regions 58. That is, the zones of extensibility 56 have a first lower deformation modulus, M1, which is lower than the second deformation modulus, M2, of the intermediate regions 58.

It should be understood that the embodiment shown in FIGS. 1–3 is a preferred embodiment, and that there may be variations of the structure illustrated that have either fewer, or additional regions with different bending or deformation properties. For instance, in the embodiments shown in FIGS. 9, 11–14, and 16, the side wrapping elements 50 may also be provided with stiffer end regions 100 that are located longitudinally outboard of the zones of extensibility 56 to prevent the panty elastics from undesirably flipping over the ends of the side wrapping elements 50. Preferably, the stiffer regions 100 of the side wrapping elements 50 have the same bending modulus as the intermediate regions. However, the bending modulus of the stiffer regions 100 may be more or less as long as the bending modulus of these regions is large enough to prevent the undesirable flipping of the ends of the side wrapping elements 50. There may also be other ways to describe the properties of the embodiment shown in FIGS. 1–3. For example, the zones of extensibility 56 can be considered to comprise fourth regions which have a fourth bending modulus which is preferably lower than the second regions 92, and possibly even lower than that of the third regions 94.

The garment surface 20B of the sanitary napkin 20 may include, and preferably does include, fasteners for attaching the sanitary napkin to the wearer's undergarment. FIGS. 1 and 2 show the central pad fastener 44 which is adapted to secure the main body portion 21 of the sanitary napkin to the crotch region of an undergarment. Any types of fasteners known in the art, such as adhesive fasteners and mechanical fasteners can be used. Fasteners comprising adhesives have been found to work well for this purpose, with pressure-sensitive adhesives being preferred. FIG. 1 shows a preferred arrangement which utilizes a pair of spaced apart longitudinally-oriented strips or zones of adhesive 44 that are centered about the longitudinal centerline L. Before the sanitary napkin 20 is placed in use, if an adhesive fastener is used, the adhesive is typically covered with a removable cover strip or release liner in order to keep the adhesive from sticking to a surface other than the crotch portion of the panty prior to use. Suitable release liners are described in the U.S. Pat. No. 4,917,697. A particularly preferred release liner which also serves as an individual package for wrapping the sanitary napkin is described in U.S. Pat. No. 4,556,146 issued to Swanson, et al.

Figure 4:
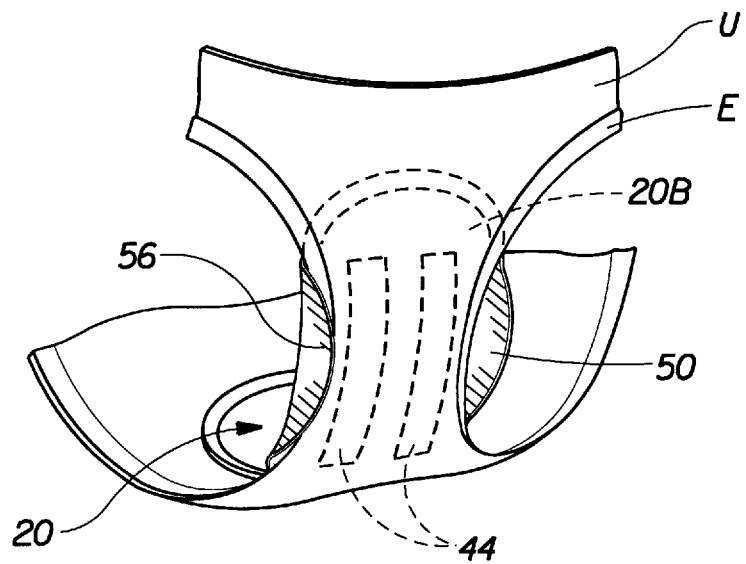
FIG. 4 is a perspective view of a portion of a panty with the sanitary napkin of the present invention in place with the side wrapping elements folded around the side edges of the wearer's panties.

The sanitary napkin 20 of the present invention is used by removing any release liner and thereafter placing the sanitary napkin 20 in a panty as shown in FIG. 4 so that the central pad fastening adhesive (or other fastener) 44 contacts the panty and maintains the sanitary napkin in position within the panty during use. The side wrapping elements 50 automatically fold along the sides of the wearer's panties by the simple action of the wearer pulling up her panties. The side wrapping elements 50 then assume an in-use position, one nonlimiting example of which is shown in FIG. 4.

Figure 5:
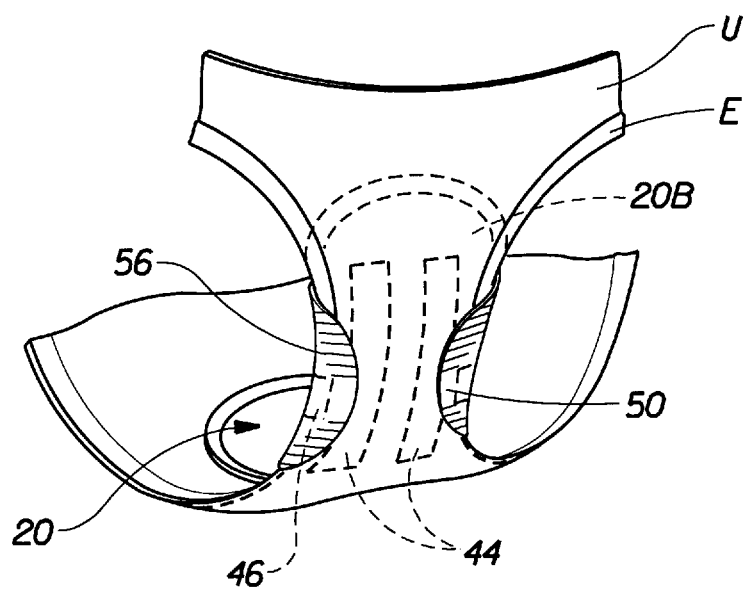
FIG. 5 is a perspective view of a portion of a panty with the sanitary napkin of the present invention in place with the side wrapping elements affixed to the underside of the wearer's panties.

FIG. 1 shows that the sanitary napkin 20 can also be provided with optional fasteners on the side wrapping elements 50. FIG. 1 shows that the longitudinally-oriented zones of adhesive may optionally have a central lateral extension 46 of adhesive (one of which is shown in FIG. 1). The central lateral extension 46 serves to adhere the side wrapping elements 50 to the undergarment. The central lateral extension 46 of adhesive maintains the side wrapping elements 50 around the elasticated edges of the crotch portion of the wearer's undergarments during vigorous motions by the wearer (although such extensions of the fasteners are generally not required under normal circumstances). The central lateral extension 46 of fastener adhesive can serve to secure the side wrapping elements 50 to the top of the wearer's panties, and/or to the underside of the wearer's panties as shown in FIG. 5. The side wrapping elements 50 can be secured to the underside of the wearer's panties by the wearer, or this can happen automatically when the wearer's thighs press the side wrapping elements 50 against the underside of the panty crotch, especially when the wearer's thighs are relatively large. The central lateral extensions 46 are preferably located in the stiffer intermediate regions 58 of the side wrapping elements 50. The central lateral extensions 46 are preferably contiguous with the longitudinally-oriented zones of adhesive, although this is not required. The presence of the intermediate region 58 provides an advantage in constructing embodiments that are provided with such central lateral extensions of adhesive. Since there is no need to provide the intermediate region 58 with extensibility, it is typically not corrugated so that it is easier to apply an adhesive-type fastener to the garment-facing side of the intermediate region 58.

Figure 6:
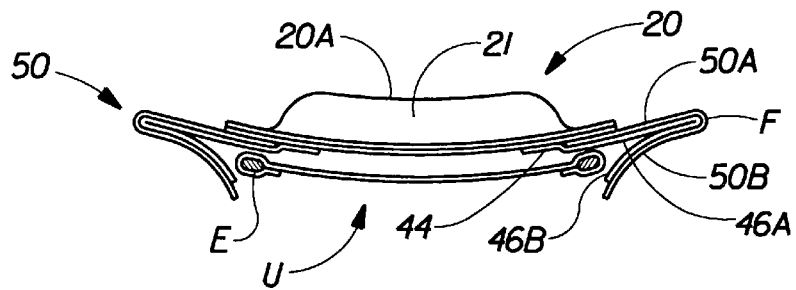
FIG. 6 is a schematic side view showing one way in which the side wrapping elements of the sanitary napkin might fold around and pinch the edge of a wearer's panties when the adhesive fastener on the undergarment-facing side extends out onto the side wrapping elements.

FIG. 6 shows a phenomenon that may occur when the sanitary napkin is provided with side wrapping elements that have fasteners with central lateral extensions 46. The side wrapping elements 50 are shown as folding around a side edge E of a crotch portion of a wearer's undergarment, U, at a longitudinally-oriented fold line F. It has been found that the central lateral extensions 46 can be of such a size and configuration that when the sanitary napkin is worn in narrow panty crotches, the fold line F divides the central extensions 46 into two portions comprising a first portion 46A and a second portion 46B. In such cases, the fold line is disposed far enough outboard of the side edge of the crotch portion of the undergarment so that a portion of said side wrapping element 50 comprising first and second portions 50A and 50B, respectively, of the side wrapping element 50 with the adhesive portions 46A and 46B thereon overlap and adhere to each other outboard of the side edge of said undergarment so that the side wrapping element forms a structure which can "grasp" or "pinch" the longitudinal edge of the panty crotch. This not only assists in maintaining the side wrapping elements 50 around the panty crotch when the panties are in place against the wearer's body, but also maintains the side wrapping elements 50 in position when the wearer pulls her panties down to check the sanitary napkin.

The operation of the side wrapping elements 50 utilized on the present invention is distinguishable in several aspects from that of conventional side flaps. First, placing a sanitary napkin having conventional flaps in a pair of panties and pulling up the panties will not consistently provide the automatic sustained wraparound feature of the present invention. There are several reasons for this. Conventional flaps are not provided with resistance to crumpling so that they will tend to crumple in use, particularly when the wearer's thighs exert compressive forces on the flaps. Conventional flaps are also not provided with zones of extensibility, so they will generally not wrap around and conform to the panties. In those cases where conventional flaps do wrap around the panties, since conventional flaps do not have zones of extensibility they will not consistently stay wrapped. Second, conventionally-sized flaps will have excess flap material that hangs down underneath the panties during wear. This material can move around excessively underneath the panties and be uncomfortable for the wearer. The side wrapping elements of the present invention, on the other hand, have a span that is ideally just wide enough to wrap around the elastic-containing edges of the panties, but no wider, avoiding the problems associated with excess flap material.

Numerous alternative embodiments of the present invention are possible. For example, the side wrapping elements are preferably mirror images of each other, and are symmetrical about the longitudinal centerline. However, it should be understood that the shape and location of the side wrapping elements described herein are those of a preferred embodiment, and other embodiments are also possible. For example, while the side wrapping elements 50 are shown as extending from each longitudinal edge of the main body portion, there may only be one side wrapping element extending from one of the edges of the main body portion. Further, the side wrapping elements 50 may be offset along the longitudinal centerline more towards one end edge of the main body portion than the other.

Figure 7:
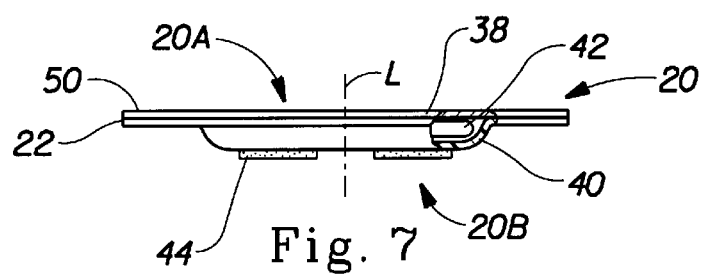
FIG. 7 is an end view of an alternative embodiment of the sanitary napkin shown in FIG. 1 in which the side wrapping elements are aligned with the plane of the body surface of the sanitary napkin.
Figure 8:
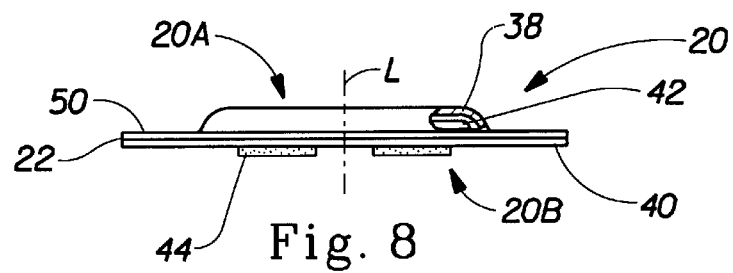
FIG. 8 is an end view of another alternative embodiment of the sanitary napkin shown in FIG. 1 in which the side wrapping elements are aligned with the plane of the garment-facing surface of the sanitary napkin.

The side wrapping elements may, in addition, extend outward from a variety of different areas of the main body portion 21. FIG. 2 shows an example of a sanitary napkin having side wrapping elements 50 that extend from a plane which is located approximately midway between the plane of the body side 20A of the main body portion of the sanitary napkin and the plane defined by the garment-facing side 20B of the main body portion 21. FIG. 7 provides an example of a sanitary napkin having side wrapping elements 50 that extend from the same plane as the body side 20A of the main body portion 21. FIG. 8 provides an example of a sanitary napkin having side wrapping elements 50 that extend from the same plane as the garment-facing side 20B of the main body portion 21.

The sanitary napkin 20 may also be provided with a variety of other types of hinge structures. For example, instead of comprising the crimped seal area shown in FIGS. 1–3, the hinge can comprise an unsealed region of a laminate structure, or a mechanically altered region of the side wrapping elements.

Figure 9:
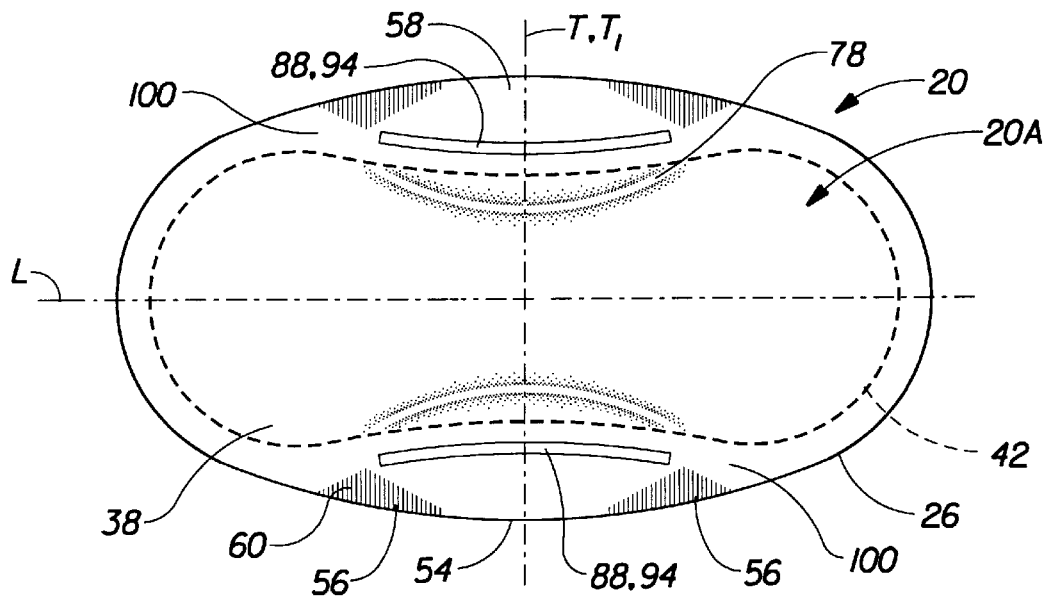
FIG. 9 is a top view of a slightly modified alternative embodiment of the sanitary napkin shown in FIG. 1.

FIG. 9 shows an embodiment in which portions of the topsheet 38 and the backsheet 40 that extend beyond the edges of the absorbent core 42 to form side wrapping elements 50 are preferably laminated together, such as by adhesives, over generally their entire inwardly-facing surfaces, except for the arcuate regions 88. The bending zones 94 in this case, comprise the arcuate regions 88. The arcuate regions 88 are provided with greater flexibility than the laminated portions of the side wrapping elements 50 because the portions of the topsheet 38 and backsheet 40 that lie within the arcuate regions 88 each flex independently as single layer components. FIG. 9 shows that the sanitary napkin (that is, the main body portion thereof) can also be provided with optional side channels 78 such as those described in U.S. Pat. No. 5,308,346 issued to Sneller, et al. Side channels 78 can be similarly provided on any of the embodiments described herein.

Figure 10:
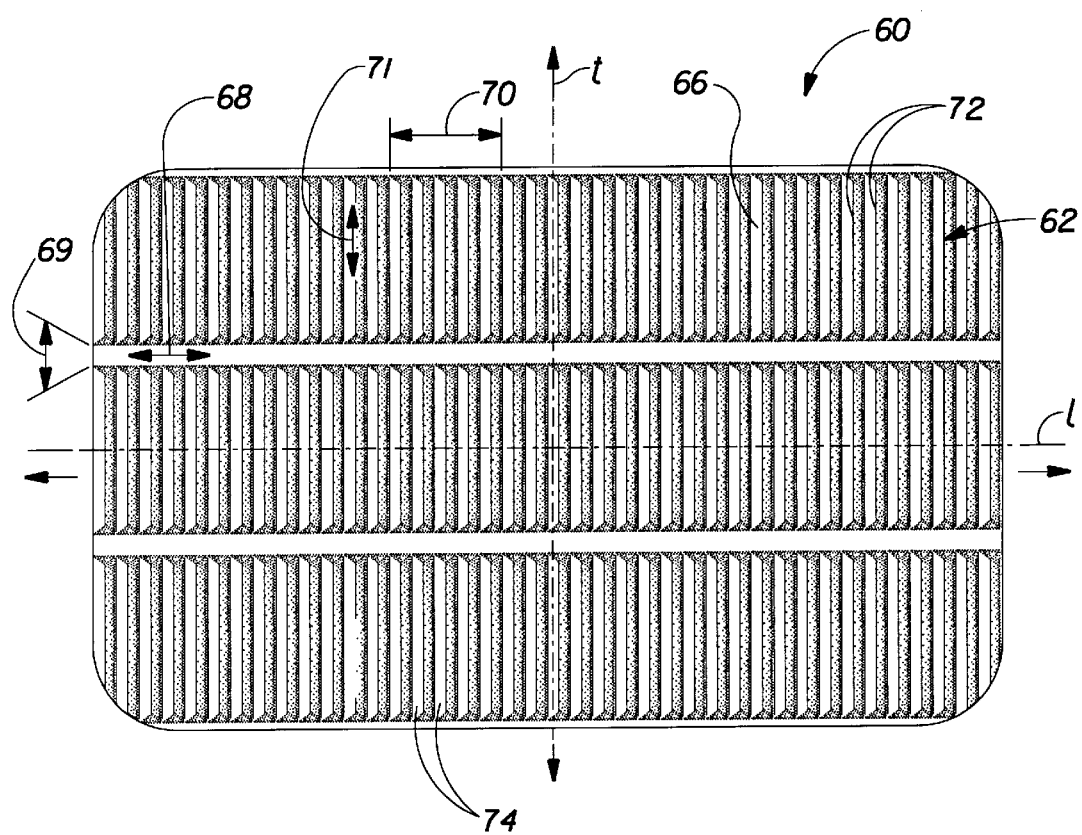
FIG. 10 is a top plan view of a web material having a strainable network of the type used in the bending zones of the sanitary napkin embodiments shown in FIGS. 11, 12, 14, and 15.
Figure 10C:
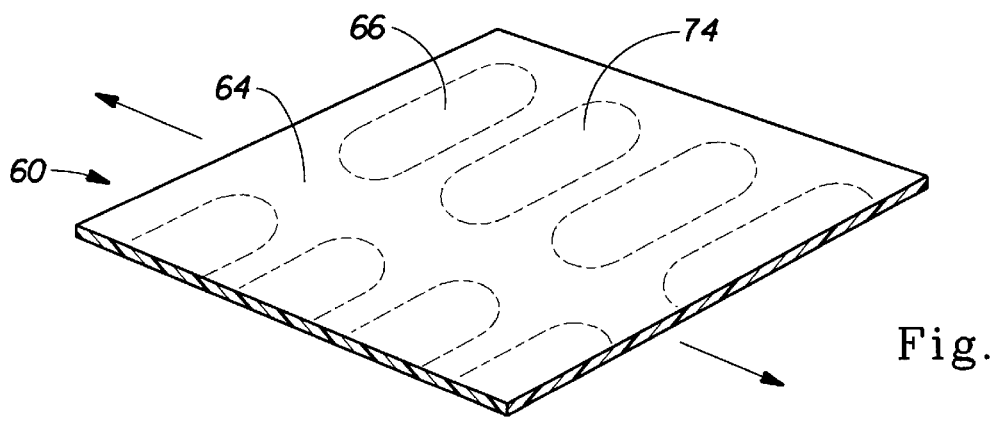
FIG. 10C is a segmented perspective illustration of the polymeric web material of FIG. 10 in a tensioned condition in which it exhibits a second stage of resistive forces to applied elongation.
Figure 11:
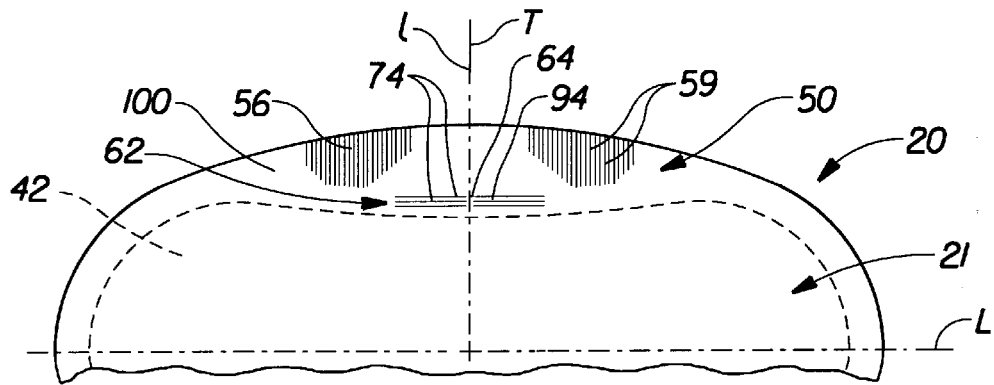
FIG. 11 is a top plan view showing a portion of a sanitary napkin which has a type of hinge structure comprising portions of the side wrapping elements that have a strainable network formed therein.

FIGS. 11–16 show several examples of sanitary napkins having hinge structures formed by mechanically altered portions of the side wrapping elements 50. FIG. 11 shows a hinge structure 94 which comprises a short, linear, longitudinally-oriented, mechanically-deformed region that is located adjacent the central region of the main body portion. The sanitary napkin 20 (or side wrapping elements 50) can be provided with mechanically deformed regions in any suitable manner that provides a hinge structure with increased flexibility and that does not result in tearing of any portions of the sanitary napkin. It has been found that many processes for providing the sanitary napkin with extensibility are particularly suitable for providing selected regions of the side wrapping elements 50 with enhanced flexibility. The hinge structure 94 of the side wrapping element 50 can, for instance, be ring rolled, or more preferably, as shown in FIG. 11, formed so that is has a strainable network region therein, or "SELFed". The SELFing process and structures formed thereby are described in greater detail below in conjunction with FIGS. 10–10C.

These structures (ring rolled structures and SELF structures) are especially preferred because the alternating ridges and valleys can form a plurality of flexible bending axes for the side wrapping elements 50. The structures also provide the flexible bending zones 94 with a degree of extensibility. The extensibility allows the portions of the side wrapping elements 50 in the bending zones 94 to expand slightly in the transverse direction to better fold around the curved sides of the wearer's panty crotch. Providing a bending zone by SELFing is additionally preferred because the unformed less extensible bands 64 of the strainable network will serve like "beams" that tend to provide the formed regions with slightly more integrity so the side wrapping elements 50 will be less likely to droop excessively at the hinge structures 94.

The process of forming a strainable network in a material or a laminate of materials such as the side wrapping elements 50 is referred to form convenience as forming a Structural Elastic-Like Film or "SELF" material because the base material into which the strainable network is formed is often a film (or has at least one component which is a film). The SELFing process is preferred for providing the side wrapping elements 50 with a bending zone 94 because (like ring rolling) such an operation can be readily adapted for use in high speed manufacturing operations. Further, the process of forming a strainable network in a material is highly preferred because it can be adapted to produce a virtually unlimited number of patterns to tailor the configuration and characteristics of the bending zone 94.

Figure 10A:
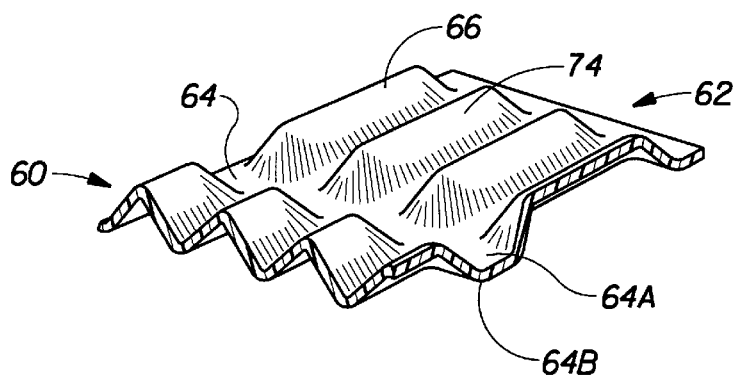
FIG. 10A is a segmented perspective illustration of the polymeric web material of FIG. 10 in an untensioned condition.
Figure 10B:
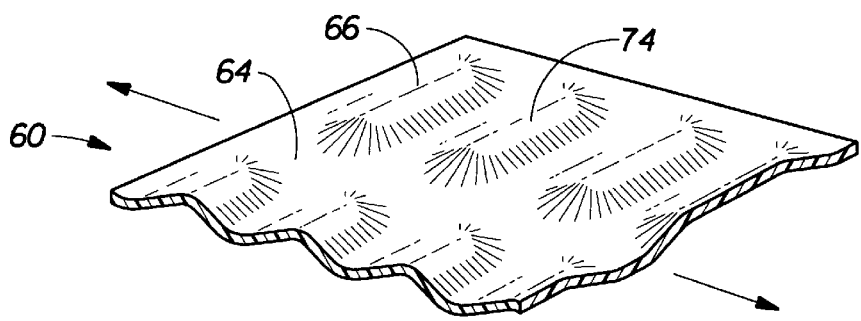
FIG. 10B is a segmented, perspective illustration of a polymeric web material of FIG. 10 in a tensioned condition in which it exhibits a first stage of resistive forces to applied elongation.

The characteristics of the strainable network 62 of a SELFed region will be discussed with reference to FIGS. 10–10C. FIGS. 10–10C show enlarged views of a web material 60 having a strainable network 62 formed therein. The term "strainable network", as used herein, refers to an interconnected and interrelated group of regions which are able to be extended to some useful degree in a predetermined direction. FIGS. 10 and 10A show the web material 60 in an untensioned condition. The strainable network 62 comprises at least two distinct and dissimilar regions. These comprise at least a first region 64 and a second region 66.

In the simplified embodiment shown in FIGS. 10 and 10A, the strainable network 62 includes a plurality of first regions 64 and a plurality of second regions 66. As shown in FIGS. 10 and 10A, the first regions 64 are substantially planar regions. That is, the material within the first region 64 is in substantially the same condition before and after the formation step undergone by web material 60. The second regions 66 include a plurality of continuous, interconnected, deformations 74 which extend alternately beyond the plane of both the first and second surfaces (64A and 64B, respectively) of the first region 64. In other embodiments, the deformations 74 may extend beyond the plane of only one of the first 64A or the second 64B surfaces of the first region 64.

FIG. 10 shows that the web material 60 having the strainable network 62 formed therein has a longitudinal centerline (or axis), 1, and a lateral centerline (or axis), t. In the sanitary napkin embodiment shown in FIG. 11, the longitudinal centerline, 1, of the strainable network is shown as being rectilinear and generally oriented in the transverse direction. However, the longitudinal centerline, 1, is not limited to such a configuration and orientation. The longitudinal centerline, 1, can be rectilinear, curvilinear, or partially rectilinear and partially curvilinear. The longitudinal centerline, 1, of the strainable network 62 can also be oriented in other directions, if desired.

FIG. 10 shows that the first regions 64 of the strainable network 62 have a first axis 68 and a second axis 69, wherein the first axis 68 is preferably longer than the second axis 69. In the simplified embodiment shown, the first axis 68 of the first region 64 is substantially parallel to the longitudinal axis, 1, of the strainable web material 60 while the second axis 69 is substantially parallel to the transverse axis, t, of the strainable web material 60. The second regions 66 of the strainable network 62 also have a first axis 70 and a second axis 71. The first axis 70 of the second region 66 is substantially parallel to the longitudinal axis 1 of the web material 60, while the second axis 71 is substantially parallel to the transverse axis t of the web material 60. In the version of the web material shown in FIGS. 10 and 10A, the first regions 64 and the second regions 66 are substantially linear, extending continuously in a direction substantially parallel to the longitudinal axis 1 of the strainable web material. In other embodiments, the second regions 66 can be curvilinear, or partially rectilinear and partially curvilinear.

While the enhanced flexibility of the SELFed region is of primary interest in the bending zone 94, the SELF structure also provides a portion of the side wrapping element 50 with a degree of extensibility. FIGS. 10A, B, and C show the manner in which the web material 60 with the strainable network 62 may exhibit at least two significantly different stages of controlled resistive force to elongation when subjected to an applied elongation in a direction parallel to a predetermined axis. The strainable network 62 exhibits first resistive forces to the applied elongation (which develop between the stage shown in FIG. 10A and the stage shown in FIG. 10B). The first resistive forces occur until the elongation of the web is sufficient to cause a substantial portion of the second regions 66 to enter the plane of applied elongation, as shown in FIG. 10B. After the web material 60 reaches the stage shown in FIG. 10B, it exhibits second resistive forces to further elongation (as illustrated by FIG. 10C). Typically, when used in regions of the side wrapping elements 50 described herein, the web material will be within the first stage of resistance to elongation so the various portions of the strainable network 62 will only extend to the stage shown in FIG. 10B and adjust so as to relax back to the stage shown in FIG. 10A.

The SELFed region of the side wrapping elements 50 is created by forming the strainable network 62 into the web material 60. As used herein, the term "forming" refers to the creation of a desired structure or geometry upon the web material 60 that will substantially retain the desired structure or geometry when it is not subjected to any externally applied elongations or forces. Suitable methods for forming a strainable network into a web material include, but are not limited to embossing by mating plates or rolls, thermoforming, high pressure hydraulic forming, and casting.

The laminate (or other web) comprising the side wrapping elements 50 into which the strainable network 62 is formed can comprise a base material (or laminate) that has a relatively low extensibility under the forces that the sanitary napkin is normally subjected to when worn. When the strainable network 62 is formed therein, however, the base material can be made extensible under pre-selected forces such as those that the sanitary napkin is normally subjected to when worn.

The depth and number of deformations 74 in the strainable network 62 can be varied to control the applied force or elongation required to extend the SELFed regions of the side wrapping elements 50. In one embodiment, the deformations 74 are formed by two rigid plates having outer dimension of 5.0" by 12" by 0.75" (12.7 cm by 30.5 cm by 2 cm). On one surface of each plate are a series of meshing teeth which are substantially triangular in cross section and measure 0.030" (0.76 mm) at their bases and taper to a vertex with a radius of 0.008" (0.2 mm) at the top. The centerlines of the teeth are spaced evenly and at 0.030" (0.76 mm) increments. On the "toothed" side of one plate, a series of grooves are cut which are parallel to each other and perpendicular to the evenly spaced teeth. These grooves measure 0.031" (0.8 mm) wide and are continuous over the entire length of the plate, and are spaced at a distance of 0.25" (6.4 mm) on center. These grooves correspond to the undeformed regions of the base material. The preferred base material is placed between the plates in a hydraulic press having platens larger than the plates to evenly distribute pressure. The plates are compressed under a load of at least 4,000 pounds (1,800 Kg). The formed web material is then removed from between the plates. The available stretch or elongation is increased if for a given number of deformations, the height or degree of deformation imparted to the web material is increased. Similarly, the available stretch or elongation is increased if for a given height or degree of deformation, the number or frequency of deformations is increased. The mating plates can be configured to create any of the patterns for the hinge structures 94 on the sanitary napkins shown in the drawings.

Figure 12:
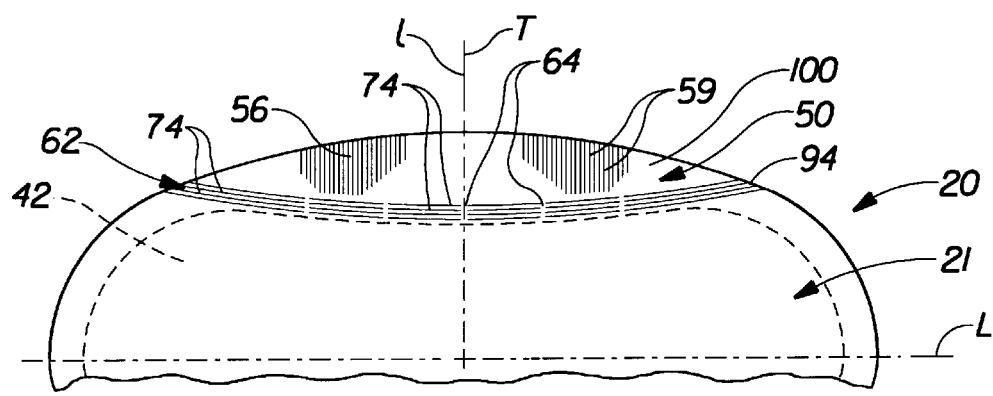
FIG. 12 is a top plan view showing a portion of a sanitary napkin which has another alternative type of hinge structure.

FIG. 12 shows a hinge structure 94 which comprises a concave region of a side wrapping element 50 that also extends generally in the longitudinal direction. FIG. 12 shows an example of an embodiment where the hinge region 94 extends the entire length of the juncture of the side wrapping element with the main body portion. The hinge structure 94 shown in FIG. 12 is preferably formed by SELFing the desired concave region of the side wrapping element 50. The concave region is formed so that the ridges defined by the deformations 74 of the strainable network of the formed region are curvilinear. The deformations 74 are oriented in same direction as boundaries of the concave region (that is, in the same direction as the edges of the hinge regions 94).

Figure 13:
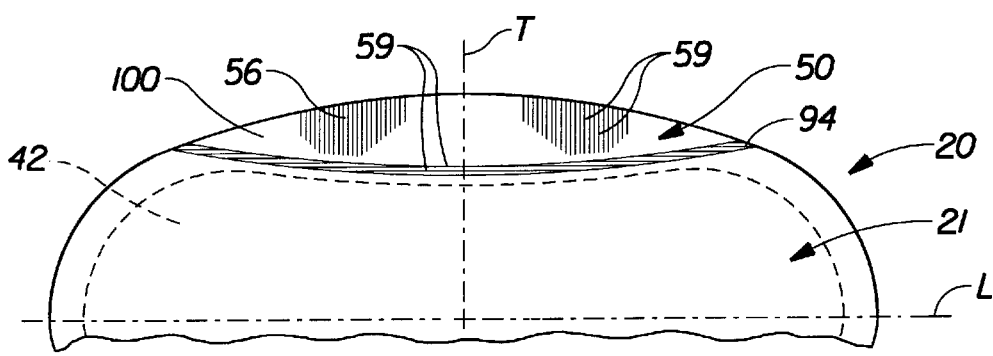
FIG. 13 is a top plan view showing a portion of a sanitary napkin which has another alternative type of hinge structure.

FIG. 13 shows another hinge structure 94 which comprises a concave region of the side wrapping element 50 that also extends along the juncture of the side wrapping element with the main body portion of the sanitary napkin. In the embodiment shown in FIG. 13, the hinge structure 94 is formed so that the ridges and valleys 59 oriented perpendicular to the transverse centerline T of the sanitary napkin. The ridges and valleys 59 of the corrugations are oriented at an angle to the boundaries of the concave hinge structure 94. The hinge structure shown in FIG. 13 may be formed by ring rolling the desired concave region of the side wrapping elements 50.

Figure 14:
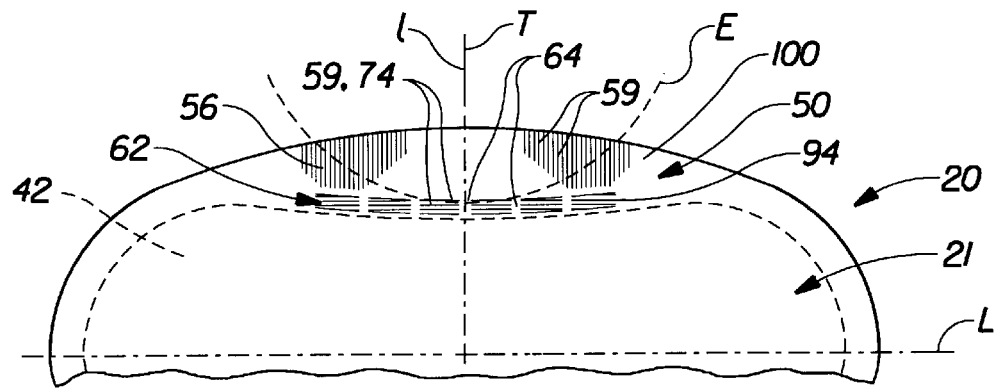
FIG. 14 is a top plan view showing a portion of a sanitary napkin which has another alternative type of hinge structure.

FIG. 14 shows a particularly preferred mechanically-deformed hinge structure 94 which combines features from some of the embodiments shown in the preceding figures. In the embodiment shown in FIG. 14, the hinge structure 94 comprises a concave SELFed region (similar to that of the embodiment shown in FIG. 12). The ridges defined by the deformations 74 of the SELFed region in FIG. 14, however, are linear and oriented in the longitudinal direction. The ridges are, thus, oriented at an angle to the boundaries of the concave region 94. In order to show where the side wrapping element 50 might fold, a dashed line, E, shows an example of where the wearer's panty elastics might be located relative to the hinge 94 and the zones of extensibility 56 when the sanitary napkin is placed in the wearer's panties. The side wrapping element 50 will preferably fold along line E. In addition, while there is no need for a crimp seal in the embodiment shown in FIG. 14 since the extensions of the topsheet and backsheet are preferably laminated together by adhesives, an embodiment can be constructed which is provided with a crimp seal, and the hinge structure 94, or at least a portion of the hinge structure 94, could be located outboard of the area of the crimp seal.

Figure 15:
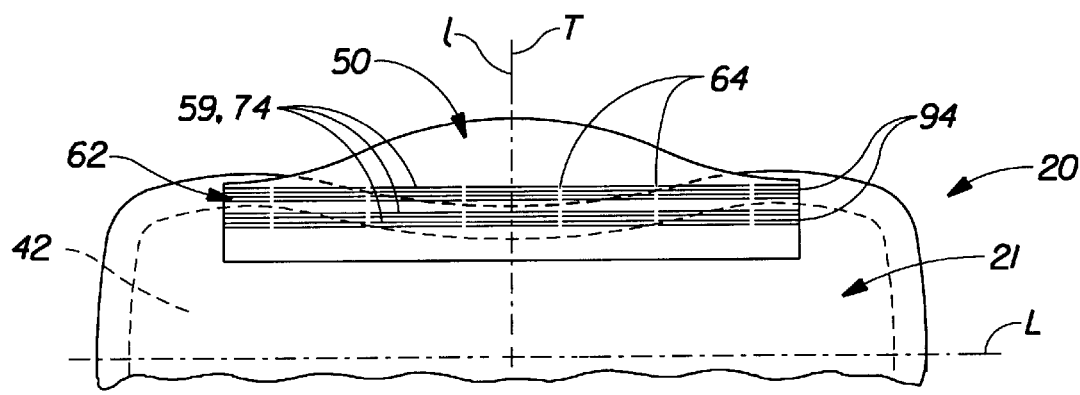
FIG. 15 is a bottom plan view showing a portion of a sanitary napkin which has another alternative type of hinge structure.

FIG. 15 shows a particularly preferred mechanically-deformed hinge structure 94 for use on embodiments in which the side wrapping elements 50 are separate elements. In the embodiment shown in FIG. 15, the side wrapping elements 50 comprise separate components that are joined to the garment-facing side 20B of the main body portion 21. The hinge structure 94 comprises a longitudinally-oriented SELFed region that extends the full length of the juncture of the side wrapping element 50 with the main body portion 21. Preferably, the hinge structure 94 comprises two spaced apart SELFed zones in which the ridges defined by the deformations 74 are oriented in the longitudinal direction. The two spaced apart SELFed zones allow the side wrapping elements 50 to fold more easily around the crotch edges of a variety of panties having a variety of different size crotch shapes and widths. FIG. 15 also shows that a substantial portion of the hinge structure 94 can be positioned underneath the main body portion 21 in such an embodiment. In addition, FIG. 15 shows that at least a portion of the hinge structure 94 may be disposed outboard of the crimp seal 48. This aids the side wrapping elements in fitting a wider variety of panty crotch sizes.

Figure 16:
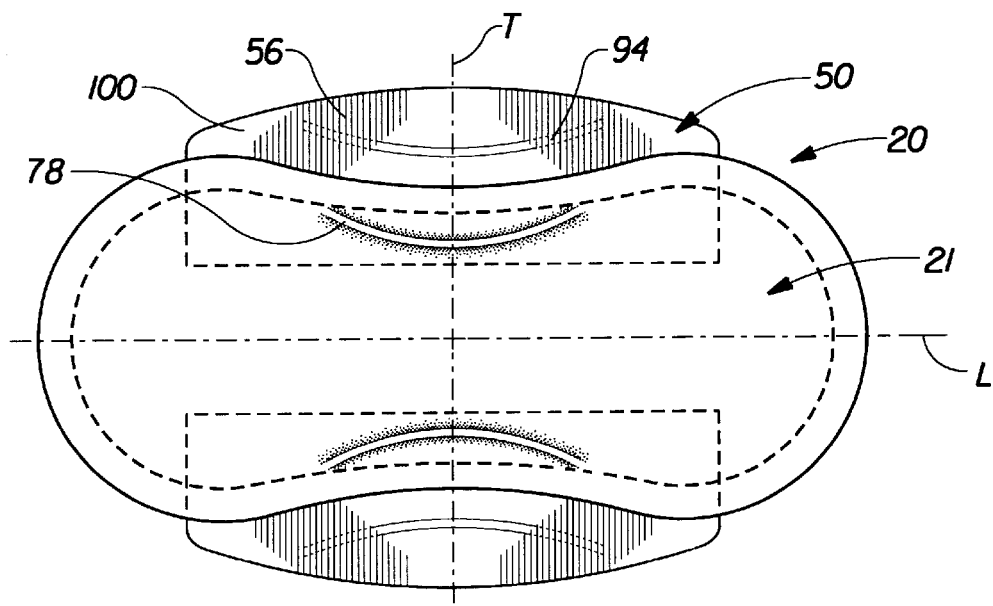
FIG. 16 is a top plan view showing a sanitary napkin which has another alternative type of hinge structure.

FIG. 16 shows another alternative hinge structure 94. In the embodiment shown in FIG. 16, the hinge structure 94 comprises a region of the side wrapping element 50 which is provided with two concentric concave score lines which are oriented side-by-side.

A virtually unlimited number of variations of the embodiments described herein are possible. For example, the hinge structure can comprise a continuous region, or a plurality of spaced apart intermittent regions. In addition, instead of only being formed of curvilinear segments or regions, the hinge structure can be comprised of rectilinear segments (or regions), curvilinear segments (or regions), or both rectilinear and curvilinear segments (or regions). Further, instead of being a separate structure from the zones of extensibility, the hinge structure and the zones of extensibility may be portions of a continuous structure. For example, the hinge structure 94 and the zones of extensibility 56 could comprise deformed areas having a configuration in which the hinge portion could gradually transition into portion of the structure that comprises the zones of extensibility. Such an embodiment might comprise continuous ridges that are arranged in the configuration of a series of concentric concave ridges and valleys. The features shown and described herein for the various embodiments can also be combined in any other suitable ways to form still more alternative embodiments.

The present invention is also applicable to other types of absorbent articles worn in the crotch region of an undergarment such as pantiliners and incontinence articles. The terms "panty liner" or "pantiliner" refer to absorbent articles that are less bulky than sanitary napkins which are generally worn by women between their menstrual periods. Suitable absorbent articles in the form of pantiliners that can be provided with the side wrapping elements described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the side wrapping elements described herein are disclosed in U.S. Pat. No. 5,300,054 issued to Feist, et al. on Apr. 5, 1994 and U.S. Pat. No. 5,304,161 issued to Noel, et al. Apr. 19, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing in a wearer's undergarment that has a crotch region with a pair of side edges, said absorbent article having a longitudinal dimension extending in a longitudinal direction and a transverse dimension extending in a transverse direction, said absorbent article comprising:

a main body portion comprising an absorbent core, said main body portion having a body-facing side, a garment-facing side, a pair of longitudinal side edges, and a periphery;

a pair of side wrapping elements for folding around the side edges of the wearer's undergarment, said side wrapping elements extending laterally outward beyond the longitudinal side edges of said main body portion a distance of less than or equal to one-half the width of said main body portion, to distal edges, said side wrapping elements having a transverse centerline that divides said side wrapping elements into opposite sides, said side wrapping elements comprising a zone of extensibility on opposite sides of said transverse centerline, and a less extensible intermediate region located between at least portions of said zone of extensibility, wherein said zone of extensibility is extensible generally in the longitudinal direction when folded around the side edges of an undergarment in an amount between about 20% and about 80% under forces of less than or equal to about 200 grams force, and said absorbent article comprises at least two regions having different bending properties, said regions comprising:

a first region located in said main body portion inboard of the longitudinal side edges of said main body portion, said first region having a first bending modulus; and a second region comprising at least a portion of said side wrapping element, said second region having a second bending modulus which is lower than said first bending modulus so that the absorbent article is provided with a discontinuity in stiffness between said first region and said second region, wherein said side wrapping element can bend about the discontinuity in stiffness between said first region and said second region.

2. The absorbent article of claim 1 wherein said discontinuity in stiffness between said first region and said second region comprises a bending zone positioned between said first region and said second region, and said bending zone comprises a third region located between a portion of the main body portion and the distal edge of the side wrapping elements wherein said third region has a third bending modulus that is lower than the bending modulus of said second region.

3. The absorbent article of claim 1 wherein said main body portion comprises a liquid pervious topsheet, a liquid impervious backsheet joined to said topsheet, and an absorbent core positioned between said topsheet and said backsheet, said absorbent core having a pair of longitudinal side edges, wherein said topsheet and backsheet each comprise an extension that extends transversely beyond the longitudinal side edges of said absorbent core to form at least part of said side wrapping elements, and said extension of said topsheet and backsheet is provided with an area of increased flexibility outboard of said longitudinal side edges of said absorbent core that serves as a hinge about which a portion of said side wrapping elements may bend.

4. The absorbent article of claim 3 wherein said area of increased flexibility comprises a densified seal where topsheet and backsheet are joined.

5. The absorbent article of claim 4 wherein at least a portion of said seal is concave relative to the distal edge of said side wrapping elements.

6. The absorbent article of claim 5 wherein said seal extends around the entire periphery of said main body portion.

7. The absorbent article of claim 3 wherein said extensions of said topsheet and backsheet have an interface therebetween, and said extensions of said topsheet and backsheet are joined together generally at their entire interface, with the exception of a generally longitudinally-oriented unbonded region that is located laterally outboard of said longitudinal side edges of said absorbent core, and said unbonded regions forms said area of increased flexibility.

8. The absorbent article of claim 7 wherein said unbonded region is concave relative to the distal edge of said side wrapping elements.

9. The absorbent article of claim 1 wherein at least one zone of extensibility comprises a region of said side wrapping element which is provided with corrugations.

10. The absorbent article of claim 1 wherein said side wrapping elements comprise separate elements that are joined to the garment-facing side of said main body portion at a point of attachment located inward of the longitudinal side edges of said main body portion, and said side wrapping elements are unattached to said garment-facing side between point of attachment and the longitudinal side edge of said main body portion.

* * * * *